United States Patent
Osborne

(10) Patent No.: US 12,083,122 B2
(45) Date of Patent: *Sep. 10, 2024

(54) LAURETH-4 CONTAINING TOPICAL FORMULATIONS

(71) Applicant: ARCUTIS BIOTHERAPEUTICS, INC., Westlake Village, CA (US)

(72) Inventor: David W. Osborne, Fort Collins, CO (US)

(73) Assignee: ARCUTIS BIOTHERAPEUTICS, INC., Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/216,089

(22) Filed: Jun. 29, 2023

(65) Prior Publication Data

US 2023/0338383 A1    Oct. 26, 2023

Related U.S. Application Data

(63) Continuation of application No. 17/443,699, filed on Jul. 27, 2021, now Pat. No. 11,730,740.

(60) Provisional application No. 63/057,503, filed on Jul. 28, 2020.

(51) Int. Cl.
| | |
|---|---|
| A61K 31/519 | (2006.01) |
| A61K 9/00 | (2006.01) |
| A61K 9/08 | (2006.01) |
| A61K 31/5377 | (2006.01) |
| A61K 31/573 | (2006.01) |
| A61K 38/13 | (2006.01) |
| A61K 47/10 | (2017.01) |
| A61K 47/20 | (2006.01) |

(52) U.S. Cl.
CPC .......... *A61K 31/519* (2013.01); *A61K 9/0014* (2013.01); *A61K 9/08* (2013.01); *A61K 31/5377* (2013.01); *A61K 31/573* (2013.01); *A61K 38/13* (2013.01); *A61K 47/10* (2013.01); *A61K 47/20* (2013.01)

(58) Field of Classification Search
CPC ...... A61K 31/519; A61K 9/0014; A61K 9/08; A61K 31/5377; A61K 31/573; A61K 38/13; A61K 47/10; A61K 47/20
See application file for complete search history.

(56) References Cited

U.S. PATENT DOCUMENTS

| | | |
|---|---|---|
| 3,711,602 A | 1/1973 | Herschler |
| 3,934,013 A | 1/1976 | Poulsen |
| 9,422,300 B2 | 8/2016 | Sun et al. |
| 9,527,851 B2 | 12/2016 | Zhang et al. |
| 10,023,577 B2 | 7/2018 | Sun et al. |
| 10,150,770 B2 | 12/2018 | Sun et al. |
| 10,428,074 B2 | 10/2019 | Zhang et al. |
| 10,786,507 B2 | 9/2020 | Lu et al. |
| 2017/0044171 A1 | 2/2017 | Zhang et al. |
| 2019/0060311 A1 | 2/2019 | Shanler et al. |
| 2019/0127364 A1 * | 5/2019 | Kozak ............ A61P 17/14 |
| 2020/0197397 A1 | 6/2020 | Arkin et al. |
| 2020/0276109 A1 | 9/2020 | Xi et al. |

FOREIGN PATENT DOCUMENTS

| | | | |
|---|---|---|---|
| WO | 2011076209 A2 | 6/2011 | |
| WO | 2019/084383 A1 | 5/2019 | |
| WO | WO-2020025910 A1 * | 2/2020 | ............ A61K 31/69 |

OTHER PUBLICATIONS

Notification Concerning Transmittal of International Preliminary Report on Patentability issued in International Application No. PCT/US2021/071019, dated Feb. 9, 2023, 7 pages.
Heather A.E. Benson "Transdermal Drug Delivery: Penetration Enhancement Techniques" Current Drug Delivery, (2005), 2(1):23-33.
David W. Osborne et al. "Skin Penetration and Permeation Properties of Transcutol®—Neat or Diluted Mixtures" AAPS PharmSciTech, (2018), 19(8):3512-3533.
Rong-Kun Chang et al. "Generic Development of Topical Dermatologic Products: Formulation Development, Process Development, and Testing of Topical Dermatologic Products" AAPS Journal, (2012), 15(1):41-52.
David W. Osborne et al. "Skin Penetration Enhancers Cited in the Technical Literature" Pharmaceutical Technology (1997), 21:58-66.
Wu-Wei Shen et al. "Effect of nonionic surfactants on percutaneous absorption of salicylic acid and sodium salicylate in the presence of dimethyl sulfoxide" J. Pharm. Sci., (1976), 65(12):1780-1783.
Bruce J. Aungst et al. "Enhancement of naloxone penetration through human skin in vitro using fatty acids, fatty alcohols, surfactants, sulfoxides and amides" International Journal of Pharmaceutics, (1986), 33(1-3):225-234.
International Search Report and the Written Opinion of the International Searching Authority, issued in corresponding International Application No. PCT/US2021/071019, dated Oct. 22, 2021, 12 pages.
Notification of Reasons for Rejection mailed Mar. 29, 2024 in corresponding Japanese Patent Application No. 2023-505843 (with English translation)(9 pages).

\* cited by examiner

*Primary Examiner* — Bahar Craigo
*Assistant Examiner* — Manahil Mirghani Ali Abdalhameed
(74) *Attorney, Agent, or Firm* — Rothwell, Figg, Ernst & Manbeck, P.C.

(57) ABSTRACT

The present invention is a method and composition comprising laureth-4 in topical formulations, wherein the laureth-4 increases the penetration of active ingredients across the skin. In a particularly preferred embodiment, the active ingredient is SHR0302.

14 Claims, 6 Drawing Sheets

LAURETH-4 CONTAINING TOPICAL FORMULATIONS

CROSS REFERENCE TO RELATED APPLICATIONS

The present application is a continuation of U.S. application Ser. No. 17/443,699, filed Jul. 27, 2021 and claims priority to U.S. Provisional Application No. 63/057,503 filed on Jul. 28, 2020, the disclosure of which is incorporated herein in its entirety by reference.

FIELD OF THE INVENTION

The subject matter disclosed herein generally relates to topical formulations containing laureth-4. Specifically, the disclosure addresses the surprising discovery that laureth-4 acts as a penetration enhancer in the presently disclosed and claimed topical formulations.

BACKGROUND OF THE INVENTION

The epidermal barrier has several functions including maintaining water balance, reducing oxidative stress, protecting against foreign substances such as microbes and antigens and protecting against ultraviolet light damage. The entire epidermis is involved in the epidermal barrier but the stratum corneum is mainly responsible for many of these functions. Many topically administered drugs do not have the ability to adequately penetrate the stratum corneum to achieve maximum clinical efficacy. In these cases, modulations of the skin penetration profiles of these drugs and skin barrier manipulations are necessary. A skin penetration enhancement can be achieved either chemically, physically or by use of appropriate formulations.

Skin penetration enhancement is achieved mechanistically by optimization of drug and vehicle properties and/or modification of the stratum corneum (H. A. E. Benson "Transdermal Drug Delivery Penetration Enhancement Techniques" Current Drug Delivery 2, 23-33, 2005). Optimization of drug and vehicle properties includes selecting the most potent active in a pharmacological class that has a molecular weight nearer 300 Daltons than 500 Daltons. Synthesis of a prodrug for actives that are too hydrophilic ($logP_{octanol/water}$<2.5), or forming ion-pairs with a charged active to facilitate partitioning into the stratum corneum are additional examples of strategies to optimize drug and vehicle properties. Similar strategies to forming ion pairs include developing eutectic systems, complexation of the drug using materials such cyclodextrins or the formulation of complex vehicles such as liposomes, vesicles or nanotechnology formulations. One of the earliest recognized strategies for optimizing topical drug and vehicle properties was the use of solvents, especially propylene glycol (PG), to balance the concentration of dissolved active in the formulation while maximizing the chemical potential, i.e. thermodynamic driving force, of the drug.

Solvents such as propylene glycol (PG), N-methylpyrrolidone (NMP), ethanol, and dimethyl sulfoxide (DMSO) have long been used to optimize drug-vehicle properties to enhance both penetration into the stratum corneum and permeation across the stratum corneum into the viable epidermis. Since 2005 diethylene glycol monoethyl ether (DEGEE) has been added to the list of solvents that optimize drug-vehicle properties of topical prescription products established by the US Food and Drug Administration as safe and effective. It has also long been recognized that these solvents readily permeate and modify the stratum corneum. Although solvents can effectively be used to enhance skin penetration/permeation of drugs, to maximize the amounts of drug that crosses the skin requires blending a solvent with fatty alcohols, fatty acids or fatty acid ester adjuvants such as nonionic surfactants.

This synergistic skin penetration was described for PG in 1976 (U.S. Pat. No. 3,934,013, Poulsen, issued Jan. 20, 1976), for NMP in 2011 (WO 2011/07629 A2, Peters son, published Jun. 30, 2011) and for DMSO in 1973 (U.S. Pat. No. 3,711,602A, Herschler, issued Jan. 16, 1973). An article published in 2018 (D W Osborne and J Musakhanian, AAPS Pharm SciTech. 19(8):3512-3533 (2018) DOI: 10.1208/s12249-018-1196-8) provided a comprehensive review of skin penetration enhancement literature of DEGEE when combined with fatty alcohols, fatty acids, or fatty acid ester adjuvants.

During review of the published skin penetration enhancer data, it becomes apparent that an in vitro permeation testing (IVPT) experimental artifact has often been mistaken for skin penetration enhancement. This artifact occurs when excised skin mounted on an in vitro diffusion cell (typically a Franz vertical diffusion cell) with an infinite dose of liquid or semisolid. For our purposes we define an infinite dose as anything over 20 µl of formulation per 1 $cm^2$ surface area of skin. The artifact is caused by the applied dose extracting barrier lipids from the stratum corneum over the time course of the experiment (typically 24 to 48-hours). Thus, the barrier properties of the tissue are reduced due to applying too much product to the surface of the skin. This results in the skin penetration enhancement factor reported for the formulation being exaggerated, sometimes by 20 to 100-fold. The magnitude of this artifact is further increased when an infinite dose is applied to excised rodent or rabbit skin compared to mounting human skin (typically dermatomed to a thickness of ~500 microns) on the IVPT diffusion cell. When applied as an infinite dose, topical solvents and fatty acid ester surfactants are the topical excipients that can greatly exaggerate IVPT flux values. Although any clinically nonrelevant dose (>20 µl) can cause this artifact, doses of 100 µl/$cm^2$ or more of a liquid or semisolid formulation containing solvents or surfactants will quickly and efficiently extract skin barrier lipids and exaggerate appearance of active in the receptor solution of the in vitro diffusion cell.

In part, because this artifact was so prevalent in the skin penetration enhancer literature of the 1980s and 1990s, the FDA Dermatology Division did not accept IVPT results as supporting data for topical product registrations prior to about 2010. In January 2012, four of the US Food and Drug Administration's key scientists published a paper entitled "Generic Development of Topical Dermatologic Products: Formulation Development, Process Development, and Testing of Topical Dermatologic Products." In that seminal publication the authors state " . . . a finite dose technique (i.e., ~3 to 5 mg/$cm^2$) is considered more relevant than infinite dose design as it better represents the clinical situation for topical drug products . . . Data generated from in vitro permeation studies using excised human skin give a good prediction of in vivo bioavailability and bioequivalence and provide a practical surrogate to clinical bioequivalence studies."

In the 1997 publication Skin Penetration enhancers Cited in the Technical Literature, laureth-4 (listed as Brij 30) had two citations, a Shen 1976 citation (WW Shen et. al. J. Pharm Sci 65(12)1780-1783 (1976) doi.org/10.1002/jps.2600651222) and an Aungst 1986 citation (B J Aungst et. al. International journal of pharmaceutics 33(1-3) 225-234

(1986) doi.org/10.1016/0378-5173(86)90057-8). Shen et. al. tested fifteen separate nonionic surfactants (10% w/w), that were incorporated into white petrolatum USP ointment base containing 10% (w/w) salicylic acid with 10% (w/w) dimethyl sulfoxide (DMSO). Percutaneous absorption was determined from blood salicylate levels in New Zealand white rabbits at regular intervals for 8 hr following application of 5.0 grams of the ointment to a 6.4×12.7 $cm^2$ area of skin. Percutaneous absorption of salicylic acid was increased significantly when sorbitan monopalmitate, sorbitan trioleate, poloxamer 231, poloxamer 182, polyoxyethylene 4 lauryl ether (laureth-4), polyoxyethylene 2 oleyl ether, or polyoxyl 8 stearate was added to the ointment containing dimethyl sulfoxide, salicylic acid, and white petrolatum. It should be noted that Shen used in vivo testing following infinite dosing to rabbit skin.

Aungst et. al. screened various chemicals as penetration enhancers by adding 10% adjuvant to propylene glycol (PG). Fatty acids and fatty alcohols were very effective promoters of naloxone flux. Maximum flux was with C12 saturated adjuvants in both the acid (235.2 $\mu g/cm^2$-hr for lauric acid) and alcohol (45.8 $\mu g/cm^2$-hr for lauryl alcohol) series, and for C18 unsaturated acid (103.0 $\mu g/cm^2$-hr for linolenic acid 18:2) and alcohol (116.3 $\mu g/cm^2$-hr for linolenyl alcohol) adjuvants. Other effective skin penetration enhancers included pelargonic acid (201.9±65.4 $\mu g/cm^2$-hr), capric acid (187.9±67.5 $\mu g/cm^2$-hr), propylene glycol laurate 43.8±5.5 $\mu g/cm^2$-hr) and laureth-4 (34.5±8.3 $\mu g/cm^2$-hr). This excised human skin experiment used infinite dosing (278 $\mu l/cm^2$) to compare 64 adjuvants for their ability to increase the in vitro flux of naloxone from PG. The control of PG alone (without added adjuvant) had a naloxone flux value of 1.6±0.4 $\mu g/cm^2$-hr.

In the 44 years since Shen first published that laureth-4 increased the percutaneous absorption of salicylic acid in rabbits, one photodynamic drug/device combination product and three topical drug products have been approved by the FDA that contain laureth-4. None of the three topical drug products use laureth-4 as a skin permeation enhancer. LAC-HYDRIN Cream (1.1% laureth-4) and LAC-HYDRIN Lotion (1.3% laureth-4) treat dry skin (xerosis) and are not designed to promote delivery past the stratum corneum, the target tissue for treating dry skin. The third approved product is VELTIN Gel (3% laureth-4), a dual-active gel that combines clindamycin phosphate and tretinoin for the treatment of acne. Laureth-4 and propylene glycol are used in this product to increase the solubility of tretinoin to 0.025%. Clindamycin phosphate is readily soluble in water without the addition of laureth-4 as a solubilizing agent. A formulator would not add a skin penetration enhancer to a topical clindamycin due to the clear warning in the VELTIN Gel label that systemic absorption of clindamycin could cause severe colitis that may result in death.

SUMMARY OF THE INVENTION

In accordance with one embodiment of the invention, it has surprisingly been discovered that the addition of laureth-4 to a topical formulation of the novel JAK inhibitor SHR0302 significantly increases the skin permeation of SHR0302. In some instances, the increase is a 5-fold to 30-fold increase in skin permeation as compared to a topical formulation without laureth-4.

In certain embodiments of the present invention, a topical pharmaceutical composition comprising a JAK inhibitor, laureth-4, and a solvent is provided. In preferred embodiments, the JAK inhibitor is SHR0302 (also known as ARQ-250).

The pharmaceutical composition can comprise a JAK inhibitor in an amount of about 0.1 to about 1.0% w/w. The pharmaceutical composition can comprise laureth-4 in an amount of about 0.5 to about 5% w/w. The pharmaceutical composition can further comprise dimethyl sulfoxide. Additionally, the pharmaceutical composition can comprise an antioxidant, a preservative, an emulsifier, a moisturizer, or a thickener.

The topical pharmaceutical composition can be selected from the group consisting of an oil-in-water emulsion, a water-in-oil emulsion, a microemulsion, a nanoemulsion, a foam, a spray, a hydrophilic ointment, or a hydrophobic ointment.

The topical pharmaceutical composition can further comprise a corticosteroid, timolol, methotrexate, or cyclosporine.

The topical pharmaceutical composition can enhance skin permeation by 5-fold to 30-fold relative to a topical pharmaceutical formulation without laureth-4 as measured by in vitro permeation testing.

In certain embodiments of the present invention, a method of treating an inflammatory skin disease, disorder, or condition in a subject in need thereof is provided. The method comprises topically administering to the subject a pharmaceutical composition comprising a JAK inhibitor, laureth-4, and a solvent.

The inflammatory skin disease, disorder, or condition can be one of atopic dermatitis, rosacea, psoriasis, seborrheic dermatitis, vitiligo, eczema, or alopecia areata.

The pharmaceutical compositions can be administered to the subject one or more times per day.

The method can comprise administration of the JAK inhibitor, SHR0302. The JAK inhibitor can be present in the pharmaceutical composition in an amount of about 0.1 to about 1.0% w/w. Laureth-4 can be present in the pharmaceutical composition in an amount of about 0.5 to about 5% w/w. The method of administration can comprise administering a pharmaceutical composition comprising dimethyl sulfoxide. Further, the pharmaceutical composition further comprising a corticosteroid, timolol, methotrexate, or cyclosporine.

The method of administration to a subject can result in skin penetration of the topical pharmaceutical composition that is enhanced by 5-fold to 30-fold relative to a topical pharmaceutical formulation without laureth-4 as measured by in vitro permeation testing.

In certain embodiments, a method for enhancing the skin penetration in a subject of a topical pharmaceutical formulation is provided. The method comprises preparing a formulation comprising a JAK inhibitor, laureth-4 and a solvent. In the method, the skin penetration of the topical pharmaceutical composition is enhanced by 5-fold to 30-fold relative to a topical pharmaceutical formulation without laureth-4.

BRIEF DESCRIPTION OF THE DRAWINGS

The accompanying drawings, which are incorporated herein and form part of the disclosure, help illustrate various embodiments of the present invention and, together with the description, further serve to describe the invention to enable a person skilled in the pertinent art to make and use the embodiments disclosed herein.

DETAILED DESCRIPTION OF THE INVENTION

Figure 1:
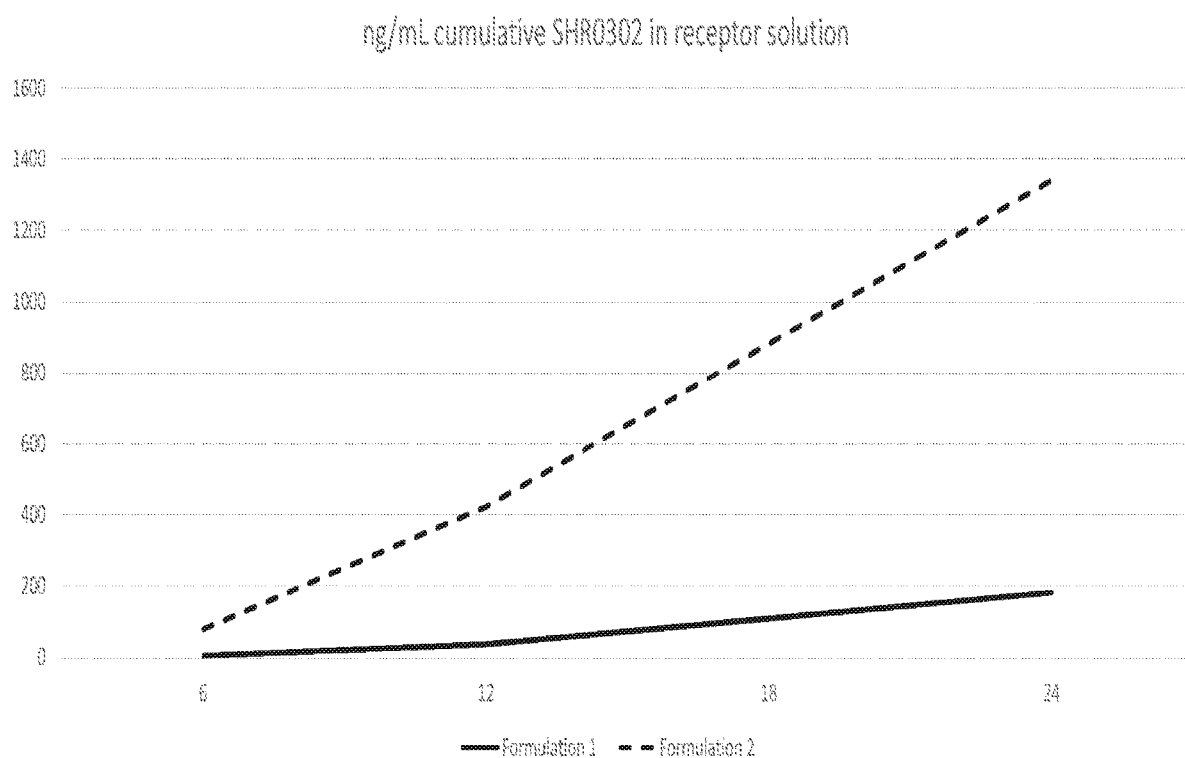
FIG. 1 illustrates IVPT results comparing an exemplary SHR0302 formulation with and without laureth-4. The x-axis depicts time (in hours) and the y-axis depicts ng/mL cumulative SHR0302 in receptor solution. The results show that the addition of laureth-4 significantly enhances the skin penetration effect in formulations containing SHR0302 and DMSO.

Before the present invention is described in detail below, it is to be understood that this invention is not limited to the particular methodology, protocols, and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

All publications, patents and patent applications cited herein are hereby incorporated by reference in their entirety unless otherwise stated. Where the same term is defined in a publication, patent, or patent application and the present disclosure incorporated herein by reference, the definition in the present disclosure represents a controlling definition. For publications, patents and patent applications referenced to describe a particular type of compound, chemistry, etc., the portion relating to such compounds, chemistry, etc. is the portion of the literature incorporated herein by reference.

Note that as used herein, the singular forms "a," "an," and "the" include plural referents unless the context clearly dictates otherwise. Thus, for example, "active ingredient" includes a single ingredient and two or more different ingredients, "solvent" refers to a single solvent and two or more different solvents or a complex mixture of solvents, and "sulfate salt" includes a single sulfate salt as well as two or more different sulfate salts.

The term "ARQ-250" or "SHR0320" refers to (3aR,5S,6aS)-N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide, and its salts unless otherwise specified.

The term "about" when used in connection with a numerical value is meant to encompass numerical values within a range having a lower limit that is 5% smaller than the indicated numerical value and having an upper limit that is 5% larger than the indicated numerical value.

"Pharmaceutically acceptable" means generally safe for administration to humans or animals. Preferably, a pharmaceutically acceptable component is one that has been approved by a regulatory agency of the Federal or a state government or listed in the U.S. Pharmacopeia, published by the United States Pharmacopeial Convention, Inc., Rockville Md., or other generally recognized pharmacopeia for use in animals, and more particularly in humans.

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

As used herein, the terms "subject" "or patient" most preferably refers to a human being. The terms "subject" or "patient" may include any mammal that may benefit from the compounds described herein.

A "therapeutic amount" or "therapeutically effective amount" is an amount of a therapeutic agent sufficient to achieve the intended purpose. The effective amount of a given therapeutic agent will vary with factors such as the nature of the agent, the route of administration, the size of the subject to receive the therapeutic agent, and the purpose of the administration. The effective amount in each individual case may be determined empirically by a skilled artisan according to established methods in the art.

The term "topical" with respect to administration of a drug or composition refers to the application of such drug or composition to the epithelial surface outside the body, including the skin or cornea. For this application, application to the inside of a body opening such as the mouth, nose or ear is not considered a topical application.

As used herein, "treat," "treating," or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

The abbreviation "w/w" represents the relative concentration of the components in the composition as "weight to weight" (i.e., percentage refers to percentage of total weight), rather than based on volume or other quantities.

Laureth-4 (CAS number 5274-68-0) also known as tetraethylene glycol monododecyl ether, 3, 6, 9, 12-tetraoxa-tetracosan-1-ol, lauryl alcohol tri(oxyethylene) ethanol, PEG-4 lauryl ether, polyethylene glycol 200 lauryl ether, polyoxyethylene (4) lauryl ether, and tetraethylene glycol dodecyl ether. The compound has the molecular formula $C_{20}H_{42}O_5$ and has a molecular weight of 362.5 g/mol. The structure of laureth-4 is as follows:

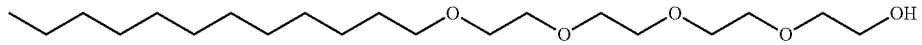 [SMILES: CCCCCCCCCCCCOCCOCCOCCOCCO]

Laureth-4 is a synthetic polymer that is commonly used as a surfactant and emulsifier in several personal care products, including cosmetics, shampoos, soaps, deodorants, and moisturizing products. For the past 45 years, laureth-4 has been known in the scientific literature as only a nominal penetration enhancer. However, in the present invention, laureth-4 surprisingly functions as a penetration enhancer. In particular, it has been surprisingly found that laureth-4 acts as skin penetration enhancer in the topical formulations of the present invention.

Janus kinase inhibitors (JAK inhibitors) are a class of compounds that function by inhibiting the activity of one or more enzymes in the JAK family (e.g., JAK1, JAK2, JAK3, or Tyk2). These compounds are thought to work by interfering with the JAK-STAT signaling pathway, which plays a central role in immune system function. Many inflammatory cytokines and other signaling molecules rely on the JAK pathway, and specifically JAK1. It has previously been shown that inhibition of JAK1 has been shown to treat a range of inflammatory diseases, including rheumatoid arthritis, psoriasis, Crohn's disease, and eczema. There is particular interest in developing topical formulations of a JAK inhibitor for the treatment of inflammatory skin conditions.

In a preferred embodiment, the JAK1 inhibitors are those disclosed in U.S. Pat. No. 9,527,851, which is hereby incorporated by reference. In a particularly preferred embodiment, the JAK1 inhibitor is (3aR,5S,6aS)-N-(3-methoxyl-1,2,4-thiadiazol-5-yl)-5-(methyl(7H-pyrrolo[2,3-d]pyrimidin-4-yl)amino)hexahydrocyclopenta[c]pyrrole-2 (1H)-carboxamide, which is also known as SHR0302 or ARQ-250. The structure of SHR0302 is:

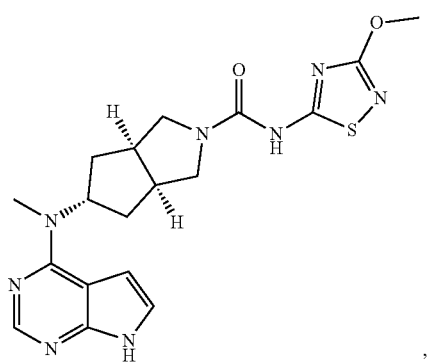 [SMILES: COc1nsc(NC(=O)N2C[C@H]3C[C@H](N(C)c4ncnc5[nH]ccc45)C[C@H]3C2)n1]

SHR0302 is a potent small molecule inhibitor of JAK 1 that has been shown to have a high selectively for JAK1 over JAK2, and thus has the potential to treat inflammatory diseases without causing the hematopoietic adverse effects, such as anemia, thrombocytopenia, and neutropenia, associated with JAK2 inhibition. It is contemplated that topical formulations comprising SHR0302 may be effective in the treatment of inflammatory skin diseases, disorders, and conditions including, but not limited to: atopic dermatitis, rosacea, psoriasis, seborrheic dermatitis, vitiligo, eczema, and alopecia areata.

It is also contemplated that other JAK inhibitors may also be useful in the treatment of inflammatory skin diseases, disorders, and conditions and thus may be incorporated into the inventive topical formulations. Examples of JAK inhibitors that may be incorporated into the inventive formulations include ruxolitinib, tofacitinib, ocalcitinib, baricitinib, peficitinib, fedratinib, upadacitinib, filgotinib, cerdulatinib, gandotinib, lestaurtinib, momelotinib, pacritinib, abrocitinib, cucurbitacin I, decernotinib, solcitinib, CHZ868, CYT387, TG101348, AZD1480, R348, VX-509, GLPG0634, SKD2586148, AC-430, BMS-911543, or PF-04965842.

The topical formulations of the present invention include a JAK inhibitor, laureth-4, and a solvent. In preferred embodiments, the JAK inhibitor is SHR0302. In preferred embodiments, the JAK inhibitor is present in an amount of about 0.01 to about 1.0% w/w, about 0.05 to about 1.0% w/w, about 0.1 to about 1.0% w/w, about 0.1 to about 0.6% w/w, or about 0.1 to about 0.5% w/w. In preferred embodiments, the laureth-4 is present in an amount of about 0.05 to about 8% w/w, about 0.1 to about 6% w/w, about 0.5 to about 5% w/w, about 1.0 to about 4% w/w.

Preferably the topical formulations of the present invention are in one of the following forms:

An oil-in-water emulsion: The product may be an emulsion comprising a discrete phase of a hydrophobic component and a continuous aqueous phase that includes water and optionally one or more polar hydrophilic excipients as well as solvents, co-solvents, salts, surfactants, emulsifiers, and other components. These emulsions may include water-soluble or water-swellable polymers that help to stabilize the emulsion.

A water-in-oil emulsion: The compositions may be an emulsion that includes a continuous phase of a hydrophobic component and an aqueous phase that includes water and optionally one or more polar hydrophilic carrier(s) as well as salts or other components. These emulsions may include oil-soluble or oil-swellable polymers as well as one or more emulsifier(s) to help to stabilize the emulsion.

A hydrophilic or hydrophobic ointment: The compositions are formulated with a hydrophobic base (e.g. petrolatum, thickened or gelled water insoluble oils, and the like) and optionally having a minor amount of a water soluble phase. Hydrophilic ointments generally contain one or more surfactants or wetting agents A microemulsion: These are clear, thermodynamically stable isotropic liquid systems that contain oil, water and surfactants, frequently in combination with a cosurfactant. Microemulsions may be water continuous, oil continuous or bicontinuous mixtures. The formulations may optionally also contain water up to 60% by weight. Higher levels may be suitable in some compositions.

A nanoemulsion: These are isotropic dispersed systems that contain water, oil, and an emulsifier. The system may be an oily system dispersed in an aqueous system, or an aqueous system dispersed in an oily system forming droplets or oily phases of nanometric sizes. Nanoemulsions often have higher loading capacity for lipophilic active ingredients than microemulsions. Hydrophobic and hydrophilic active ingredients can also be formulated in nanoemulsion. Nanoemulsions may be formed by any suitable method known in the art, including high-pressure homogenization, microfluidization, and phase-inversion temperature.

An aerosol foam or spray: The product may be an alcohol/solvent based solution containing an emulsifying wax or an emulsion comprising a discrete phase of a hydrophobic component and a continuous aqueous phase that includes water and optionally one or more polar hydrophilic excipients as well as solvents, co-solvents, surfactants, emulsifiers, and other components. These solvent or emulsion foam concentrates may include water-soluble or water-swellable polymers that help to stabilize the emulsion and corrosion inhibitors to improve compatibility between the formulation and the package. A hydrocarbon, hydrochlorofluorocarbon (HCFC) or chlorofluorocarbon (CFC) aerosol propellant can be added to the solvent or emulsion foam concentrate in packaging designed to maintain pressure until the foam or spray product is dispensed for application.

Solvents

Compositions according to the present invention may include one or more solvents or co-solvents which modify skin permeation or the activity of other excipients contained in the formulation. Solvents include, but are not limited to acetone, ethanol, benzyl alcohol, butyl alcohol, diethyl sebacate, diethylene glycol monoethyl ether, diisopropyl adipate, dimethyl isosorbide, dimethyl sulfoxide, ethyl acetate, isopropyl alcohol, isopropyl isostearate, isopropyl myristate, N-methyl pyrrolidine, polyethylene glycol, glycerol, propylene glycol and SD alcohol.

Surfactants

Compositions according to the present invention may include one or more surfactants or co-surfactants. Surfactants include, but are not limited to short-chain alcohols, alkane diols and triols, alkyl phosphate esters, polyethylene glycols and glycol ethers, polyethylene stearyl ethers, including those sold under the tradenames Brij S2, Brij S20, Brij 721, Brij 38, Brij 52, Brij 56, and Brij W1, pyrrolidine derivatives, bile salts, sorbitan fatty acid esters and polyoxyethylene sorbitan fatty acid esters.

Moisturizers

Compositions according to the present invention may include one or more moisturizers to increase the level of hydration. The moisturizer can be a hydrophilic material including humectants or it can be a hydrophobic material including emollients. Suitable moisturizers include, but are not limited to: 1,2,6-hexanetriol, 2-ethyl-1,6-hexanediol, butylene glycol, glycerin, polyethylene glycol 200-8000, butyl stearate, cetostearyl alcohol, cetyl alcohol, cetyl esters wax, cetyl palmitate, cocoa butter, coconut oil, cyclomethicone, dimethicone, docosanol, elastomers, ethylhexyl hydroxystearate, fatty acids, glyceryl isostearate, glyceryl laurate, glyceryl monostearate, glyceryl oleate, glyceryl palmitate, glycol distearate, glycol stearate, isopropyl palmitate, isostearic acid, isostearyl alcohol, lanolin, mineral oil, limonene, medium-chain triglycerides, menthol, myristyl alcohol, octyldodecanol, oleic acid, oleyl alcohol, oleyl oleate, olive oil, paraffin, peanut oil, petrolatum, Plastibase-50W, polypropylene glycol stearyl ethers, and stearyl alcohol.

Polymers and Thickeners

For certain applications, it may be desirable to formulate a product that is thickened with soluble, swellable, or insoluble organic polymeric thickeners such as natural and synthetic polymers or inorganic thickeners such as acrylates copolymer, carbomer 1382, carbomer copolymer type B, carbomer homopolymer type A, carbomer homopolymer type B, carbomer homopolymer type C, acrylamide/sodium acryloyldimethyl taurate copolymer, carboxy vinyl copolymer, carboxymethylcellulose, carboxypolymethylene, carrageenan, guar gum, xanthan gum, hydroxyethyl cellulose, hydroxypropyl cellulose, microcrystalline wax, and methylcellulose.

Additional Components

Compositions according to the present invention may be formulated with additional components such as fillers, carriers and excipients conventionally found in cosmetic and pharmaceutical topical products. Additional components including but not limited to antifoaming agents, preservatives (e.g. p-hydroxybenzoic esters, benzyl alcohol, phenylmercury salts, chlorocresol, methylparaben, propylparaben), antioxidants (e.g., BHT, BHA, ascorbic acid, tocopherol, citric acid, propyl gallate, sodium metabisulfite), sequestering agents, stabilizers, buffers, pH adjusting agents (preferably agents which result in an acidic pH, including but not limited to gluconolatone, citric acid, lactic acid, and alpha hydroxyacids), skin penetration enhancers, skin protectants (including but not limited to petrolatum, paraffin wax, dimethicone, glyceryl monoisostearate, isopropyl isostearate, isostearyl isostearate, cetyl alcohol, potassium cetyl phosphate, cetyl behenate and behenic acid), chelating agents, film formers, suspending agents (e.g., xantham gum), dyes, pigments, diluents, bulking agents, fragrances, aerosol producing agents and other excipients to improve the stability or aesthetics, may be added to the composition.

Compositions according to the present invention may be formulated with additional active agents depending on the conditions being treated. Exemplary additional active agents for a combination topical drug product include corticosteroids (e.g., clobetasol, betamethasone, halobetasol, or triamcinolone), beta andrenergic antagonists (e.g., timolol), calcineurin inhibitors (e.g., tacrolimus, or pimecrolimus), methotrexate, or cyclosporine.

Administration and Dosage

The compositions according to the present invention can be administered by any suitable administration route including but not limited to cutaneously (topically), transdermally, and mucosally. In a preferred embodiment, the composition is administered topically. The composition can be administered one or more times per month, one or more times per week, or one or more times per day. In preferred embodiments, the compositions are administered one, two, or three times per day.

The topical formulations containing laureth-4 disclosed herein can result in improved skin permeation. In some instances, the increase is a 5-fold to 30-fold increase in skin permeation as compared to the same topical formulation without laureth-4 as measured by in vitro permeation testing (IVPT). In preferred embodiments, the topical formulation containing laureth-4 products a greater than 5-fold, greater than 8-fold, greater than 10-fold, greater than 15-fold, or greater than 20-fold increase in skin permeation compared to the same topical formulation without laureth-4.

EXAMPLES

While various embodiments have been described herein, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Experimental Example 1

Formulations of the following compositions were prepared:

| Ingredients | Formulation # 1 (2019-048-55) % w/w | Formulation # 2 (2019-048-57) % w/w |
|---|---|---|
| SHR0302 | 0.5 | 0.5 |
| DMSO | 35.0 | 35.0 |
| Laureth-4 | — | 4.0 |
| Butylated Hydroxytoluene | 0.05 | 0.05 |
| Benzyl Alcohol | 2.0 | 2.0 |
| Propylene Glycol | 15.0 | 12.5 |
| PEG 200 | 15.0 | 12.5 |
| Cyclomethicone | 7.0 | 7.0 |
| Dimethicone (350 cst) | 1.0 | 1.0 |
| ST-Elastomer 10 | 2.0 | 2.0 |
| Pemulen TR 1 | 0.8 | 0.8 |
| Carbopol 974P | 1.5 | 1.5 |
| Purified Water | Q.S to 100 | Q.S to 100 |
| 25% Trolamine | pH to 5.5-5.9 | pH to 5.5-5.9 |
| 10% (w/v) HCl | pH to 5.5-5.9 | pH to 5.5-5.9 |

Experimental Example 2

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm$^2$ (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

The results of this experiment (reported as ng/mL cumulative SHR0302 in receptor solution) are shown in Table 1 and depicted in FIG. 1. The addition of laureth-4 to the topical formulation containing DMSO showed a surprising and striking increase in skin penetration when compared to a nearly identical formulation without laureth-4. These results demonstrate the efficacy of laureth-4 as a skin penetration enhancer in the inventive topical formulations.

Experimental Example 3

Formulations of the following compositions were prepared:

| Ingredient | Formulation # 3 (BR18034A) % w/w | Formulation # 4 (2019-006-27) % w/w | Formulation # 5 (2019-048-59) % w/w |
|---|---|---|---|
| SHR0302 | 0.3 | 0.3 | 0.3 |
| N-Methyl-2 Pyrriolidone | 20.0 | 20.0 | 20.0 |
| Laureth-4 | 4.0 | 0.1 | 4.0 |
| Butylated Hydroxytoluene | 0.05 | 0.05 | 0.05 |
| Methylparaben | 0.2 | 0.2 | 0.2 |
| Propylparaben | 0.05 | 0.05 | 0.05 |
| Crodafos CES | 10.0 | 10.0 | 10.0 |
| Isopropyl Palmitate | 5.0 | 5.0 | 5.0 |
| White Petrolatum (Protopet 1 S) | 5.0 | 5.0 | 5.0 |
| Propylene Glycol | 15.0 | 15.0 | 15.0 |
| PEG 200 | 15.0 | 15.0 | 15.0 |
| 1N Sodium Hydroxide | 3.5 | 3.5 | 3.5 |
| Xanthan Gum | — | 0.2 | 0.2 |
| Purified Water | Q.S to 100 | Q.S to 100 | Q.S to 100 |
| 10% Sodium Hydroxide | pH to 5.5-5.9 | pH to 5.5-5.9 | pH to 5.5-5.9 |

Experimental Example 4

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm$^2$ (8 mm in diameter) diffusion area and a receptor chamber filled with 3.0 ml of 4% BSA in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 2:
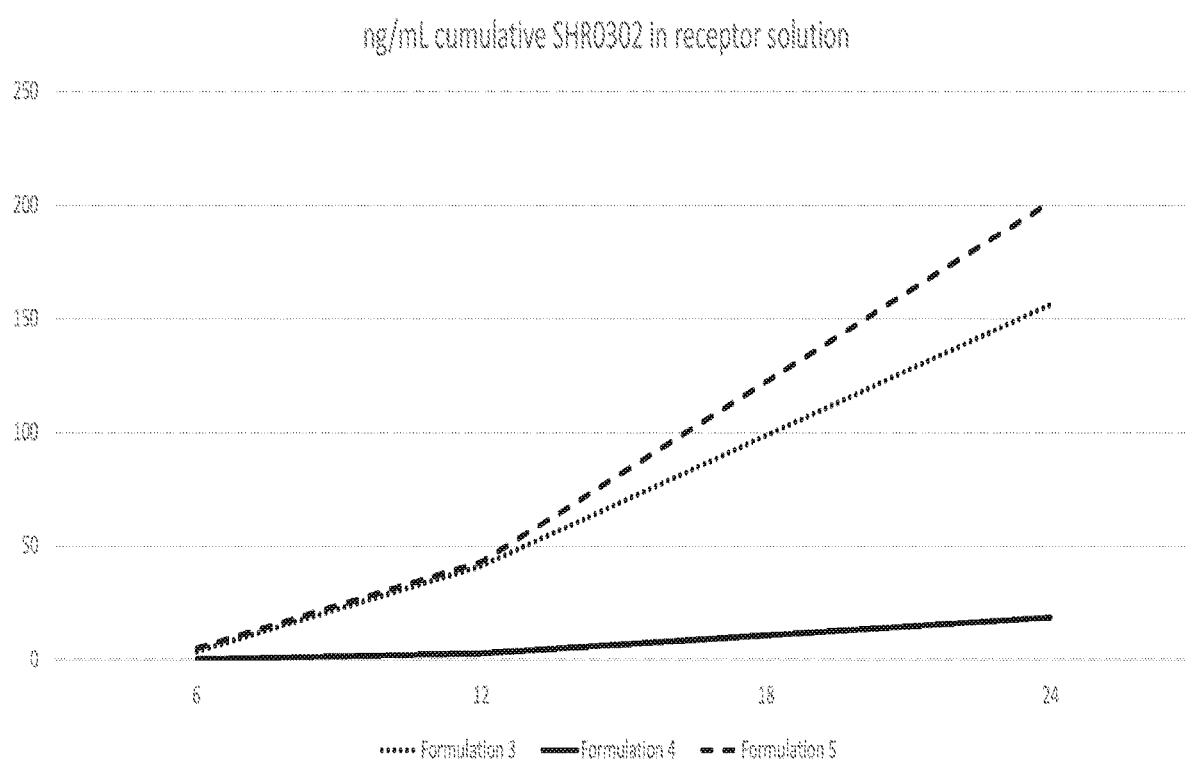
FIG. 2 illustrates IVPT results comparing three exemplary SHR0302 formulations comprising varying concentrations of xanthan gum and laureth-4. The x-axis depicts time (in hours) and the y-axis depicts ng/mL cumulative SHR0302 in receptor solution. The results show that the addition of laureth-4 significantly enhances the skin penetration effect in formulations containing SHR0302 and NMP.

The results of this experiment (reported as ng/mL cumulative SHR0302 in receptor solution) are shown in Table 2 and depicted in FIG. 2. The addition of laureth-4 to the topical formulation containing NMP showed a surprising and striking increase in skin penetration when compared to a nearly identical formulation with minimal amounts laureth-4. These results demonstrate the efficacy of laureth-4 as a skin penetration enhancer in the inventive topical formulations.

TABLE 1

| Formulation # | 1 hr | 3 hr | 6 hr | 12 hr | 24 hr | Epidermis 24 hr | Dermis 24 hr |
|---|---|---|---|---|---|---|---|
| 1 | 0.0 | 0.3 | 4.7 | 36.5 | 182.5 | 71.3 | 125.6 |
| 2 | 0.0 | 8.1 | 79.4 | 423.3 | 1340.6 | 52.9 | 435.5 |

TABLE 2

| Formulation # | 1 hr | 3 hr | 6 hr | 12 hr | 24 hr | Epidermis 24 hr | Dermis 24 hr |
|---|---|---|---|---|---|---|---|
| 3 | 0 | 0.5 | 3.5 | 41.1 | 156.4 | 15 | 63 |
| 4 | 0 | 0 | 0.1 | 2.7 | 18.4 | 33.1 | 15.0 |
| 5 | 0 | 0.6 | 4.8 | 42.8 | 201.2 | 25.9 | 62.3 |

Experimental Example 5

Formulations of the following compositions were prepared:

| Ingredients | Formulation #6 % w/w | Formulation #7 (2020-092-47) % w/w |
|---|---|---|
| SHR0302 | 0.5 | 0.5 |
| Sodium Phosphate Monobasic, Anhydrous | 0.5 | 0.5 |
| Methylparaben | 0.1 | 0.1 |
| Propylparaben | 0.02 | 0.02 |
| Dimethyl Sulfoxide | 10.0 | 10.0 |
| Dimethyl Isosorbide | 10.0 | 10.0 |
| Diethylene glycol monoethyl ether | 10.0 | 10.0 |
| Polysorbate 60 | 10.0 | 10.0 |
| Hydroxyethyl Cellulose | 0.5 | 0.5 |
| Laureth 4 | — | 4.0 |
| Crodafos CES | 10.0 | 10.0 |
| White Petrolatum | 10.0 | 10.0 |
| Dimethicone, 350 cst | 1.0 | 1.0 |
| Purified Water | Q.S. to 100 | Q.S. to 100 |

Experimental Example 6

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm² (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 3:
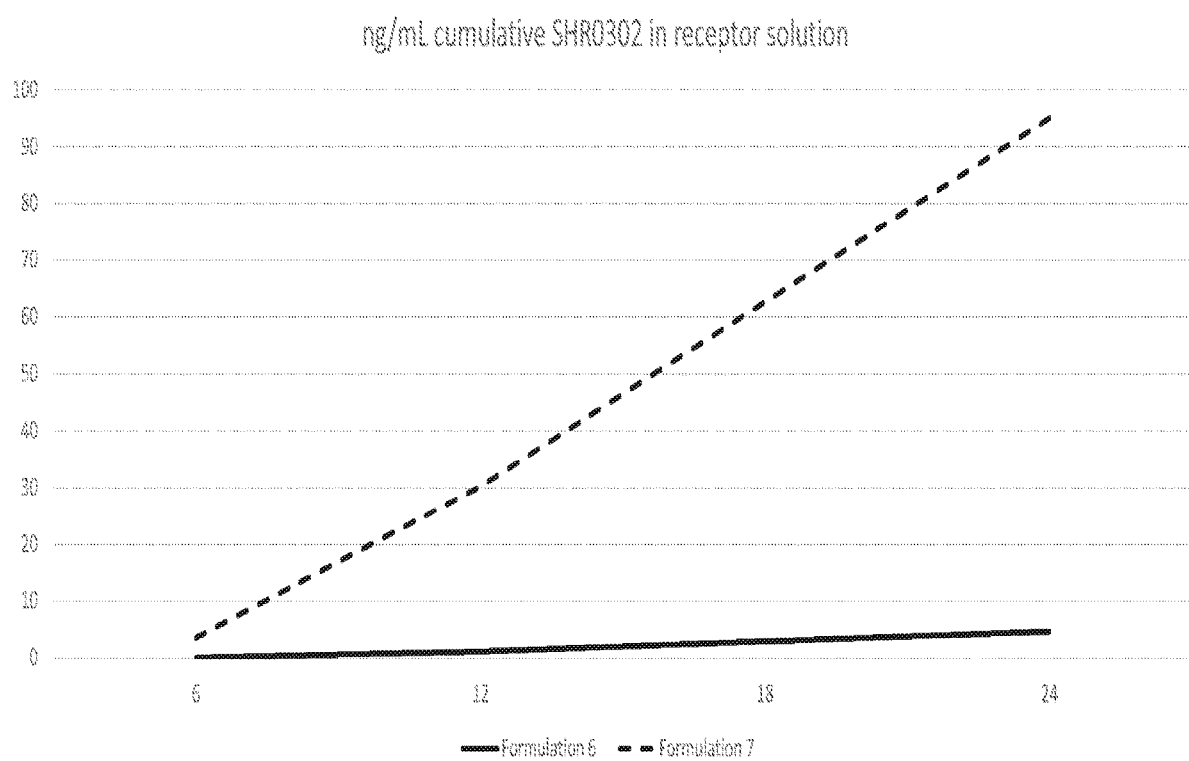
FIG. 3 illustrates IVPT results comparing an exemplary SHR0302 formulation with and without laureth-4. The x-axis depicts time (in hours) and the y-axis depicts ng/mL cumulative SHR0302 in receptor solution. The results show that the addition of laureth-4 significantly enhances the skin penetration effect in formulations containing SHR0302.

The results of this experiment (reported as ng/mL cumulative SHR0302 in receptor solution) are shown in Table 3 and depicted in FIG. 3. The addition of laureth-4 to the topical formulation containing a 1:1:1 ratio of DMSO:DMI:DEGEE showed a surprising and striking increase in skin penetration when compared to a nearly identical formulation without laureth-4. These results demonstrate the efficacy of laureth-4 as a skin penetration enhancer in the inventive topical formulations.

TABLE 3

| Formulation # | 1 hr | 3 hr | 6 hr | 12 hr | 24 hr | Epidermis 24 hr | Dermis 24 hr |
|---|---|---|---|---|---|---|---|
| 6 | 0.0 | 0.0 | 0.0 | 1.1 | 4.6 | 22.8 | 10.0 |
| 7 | 0.0 | 0.0 | 3.5 | 62.6 | 95.0 | 155.2 | 115.1 |

Experimental Example 7

Formulations of the following compositions were prepared:

| Ingredients | Formulation #8 % w/w | Formulation #9 (2020-092-61) % w/w |
|---|---|---|
| SHR0302 | 0.5 | 0.5 |
| Sodium Phosphate Monobasic, Anhydrous | 0.5 | 0.5 |
| Glycerin | 5.0 | 5.0 |
| Methylparaben | 0.1 | 0.1 |
| Propylparaben | 0.02 | 0.02 |
| Butylated hydroxytoluene | 0.05 | 0.05 |
| Dimethyl Sulfoxide | 10.0 | 10.0 |
| Dimethyl Isosorbide | 10.0 | 10.0 |
| Diethylene glycol monoethyl ether | 10.0 | 10.0 |
| Xanthan Gum | 0.2 | 0.2 |
| Laureth 4 | — | 4.0 |
| Polyethylene (2) stearyl ether | 5.0 | 5.0 |
| Polyethylene (21) stearyl ether | 5.0 | 5.0 |
| Cetostearyl Alcohol | 6.0 | 6.0 |
| PPG 15 Stearyl Ether | 5.0 | 5.0 |
| Purified Water | Q.S to 100 | Q.S to 100 |

Experimental Example 8

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm² (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 4:
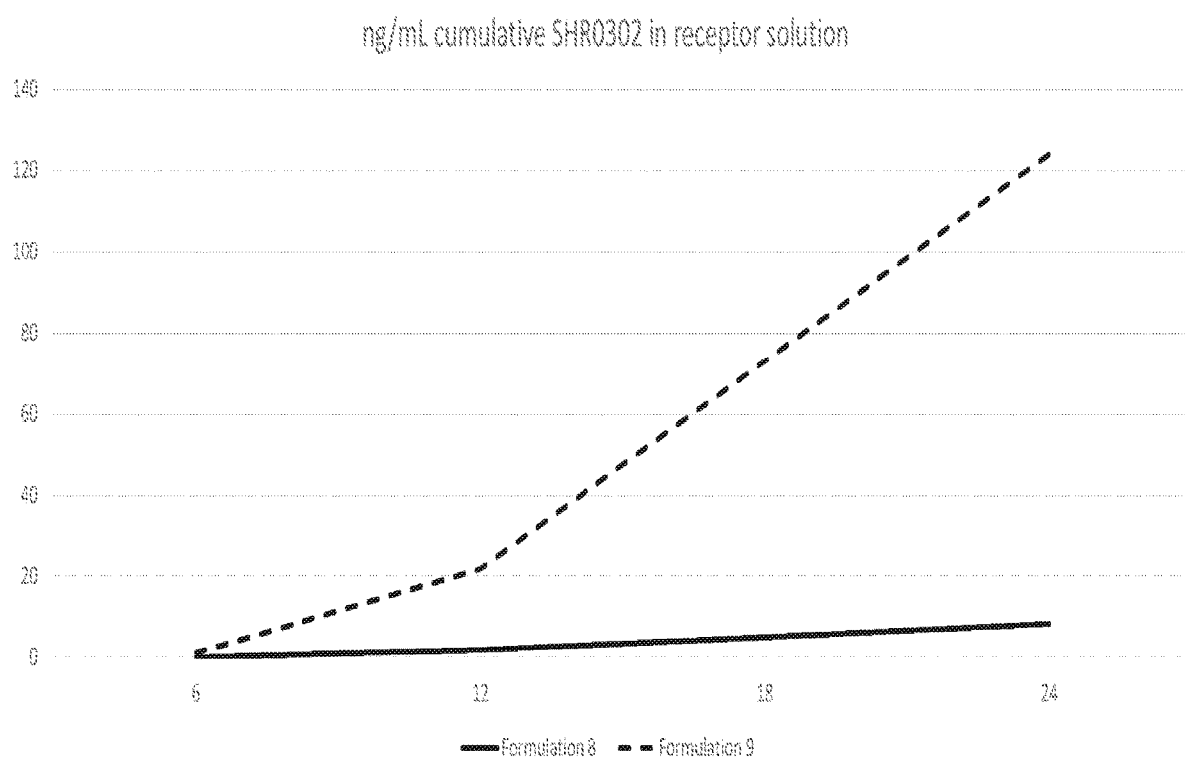
FIG. 4 illustrates IVPT results comparing an exemplary SHR0302 formulation with and without laureth-4. The x-axis depicts time (in hours) and the y-axis depicts ng/mL cumulative SHR0302 in receptor solution. The results show that the addition of laureth-4 significantly enhances the skin penetration effect in formulations containing SHR0302.

The results of this experiment (reported as ng/mL cumulative SHR0302 in receptor solution) are shown in Table 4 and depicted in FIG. 4. The addition of laureth-4 to the topical formulation containing a 1:1:1 ratio of DMSO:DMI:DEGEE showed a surprising and striking increase in skin penetration when compared to a nearly identical formulation without laureth-4. These results demonstrate the efficacy of laureth-4 as a skin penetration enhancer in the inventive topical formulations.

TABLE 4

| Formulation # | 1 hr | 3 hr | 6 hr | 12 hr | 24 hr | Epidermis 24 hr | Dermis 24 hr |
|---|---|---|---|---|---|---|---|
| 8 | 0.0 | 0.0 | 0.0 | 1.8 | 8.3 | 41.5 | 27.2 |
| 9 | 0.0 | 0.0 | 1.1 | 21.9 | 124.3 | 191.4 | 119.6 |

Experimental Example 9

Formulations of the following compositions were prepared:

| Ingredients | Formulation # 10 % w/w | Formulation # 11 % w/w |
|---|---|---|
| SHR0302 | 0.5 | 0.5 |
| DMSO | 30.0 | 30.0 |
| Laureth-4 | — | 4.0 |
| Butylated Hydroxytoluene | 0.05 | 0.05 |
| Benzyl Alcohol | 2.0 | 2.0 |
| Propylene Glycol | 15.0 | 12.5 |
| PEG 200 | 15.0 | 12.5 |
| Cyclomethicone | 7.0 | 7.0 |
| Dimethicone (350 cst) | 1.0 | 1.0 |
| ST-Elastomer 10 | 2.0 | 2.0 |
| Pemulen TR 1 | 0.8 | 0.8 |
| Carbopol 974P | 1.5 | 1.5 |
| Edetate Disodium, Dihydrate | 0.05 | 0.05 |
| D-Limonene | 0.1 | 0.1 |
| Purified Water | Q.S to 100 | Q.S to 100 |
| 25% Trolamine | pH to 4.5-5.5 | pH to 4.5-5.5 |
| 10% (w/v) HCl | pH to 4.5-5.5 | pH to 4.5-5.5 |

Experimental Example 10

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm$^2$ (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 5:
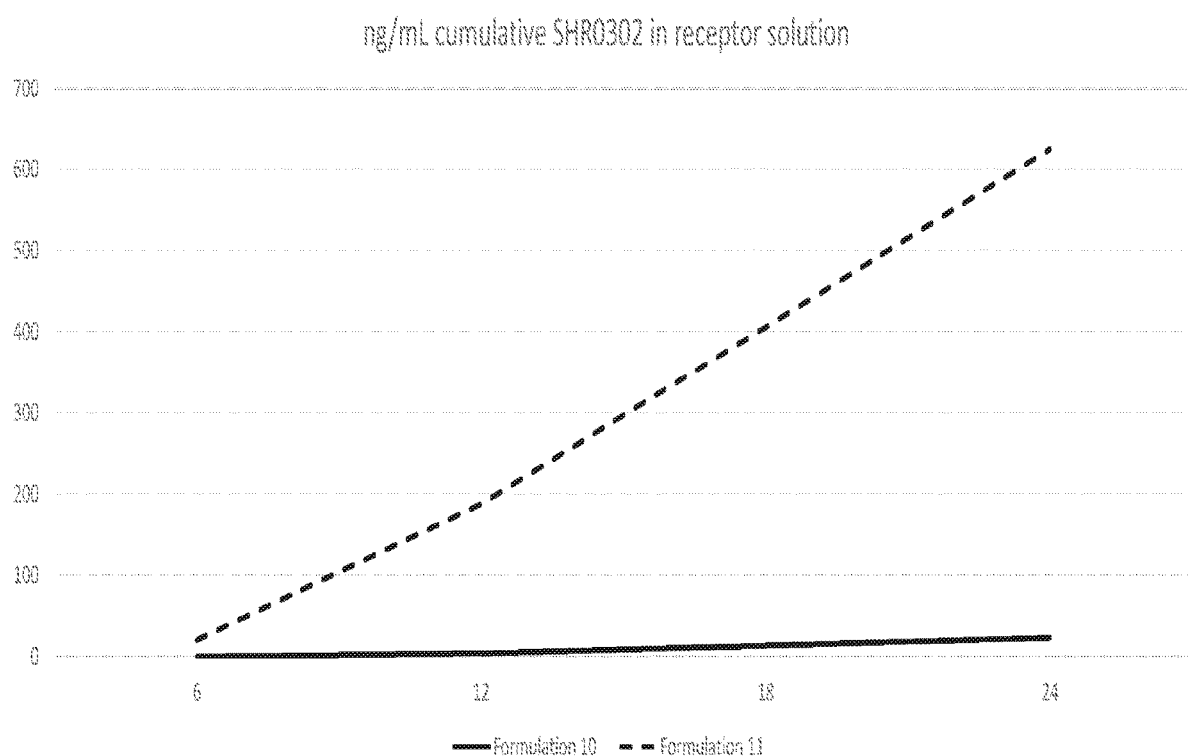
FIG. 5 illustrates IVPT results comparing an exemplary SHR0302 formulation with and without laureth-4. The x-axis depicts time (in hours) and the y-axis depicts ng/mL cumulative SHR0302 in receptor solution. The results show that the addition of laureth-4 significantly enhances the skin penetration effect in formulations containing SHR0302.

The results of this experiment (reported as ng/mL cumulative SHR0302 in receptor solution) are shown in Table 5 and depicted in FIG. 5. The addition of laureth-4 to the topical formulation containing DMSO showed a surprising and striking increase in skin penetration when compared to a nearly identical formulation without laureth-4. These results demonstrate the efficacy of laureth-4 as a skin penetration enhancer in the inventive topical formulations.

TABLE 5

| Formulation # | 1 hr | 3 hr | 6 hr | 12 hr | 24 hr | Epidermis 24 hr | Dermis 24 hr |
|---|---|---|---|---|---|---|---|
| 10 | 0.0 | 0.0 | 0.0 | 4.2 | 23.6 | 495.5 | 98.6 |
| 11 | 0.0 | 1.8 | 20.7 | 187.6 | 625.3 | 191.8 | 226.8 |

Experimental Example 11

Formulations of the following compositions were prepared:

| Ingredients | Formulation # 12 (2020-092-75) % w/w | Formulation # 13 (2020-092-74) % w/w |
|---|---|---|
| SHR0302 | 2.0 | 2.0 |
| DMSO | 98.0 | 94.0 |
| Laureth-4 | — | 4.0 |

Experimental Example 12

IVPT results comparing prototype SHR0302 formulations used excised human cadaver skin dermatomed to a target thickness of 500 microns was received frozen from a US tissue bank and stored at −20° C. until use. Skin was loaded onto vertical Franz cells having a 0.503 cm$^2$ (8 mm in diameter) diffusion area and a receptor chamber filled with 3.0 ml of 4% Bovine Serum Albumin (BSA) in water containing 0.01% gentamicin sulfate thermostated at 32° C. Using a positive displacement pipette, 5 microliters of cream was dosed on each Franz Cell (10 mg per square centimeter of skin). Appearance of the active in receptor solution (average of four replicates) was determined using LC/MS/MS.

Figure 6:
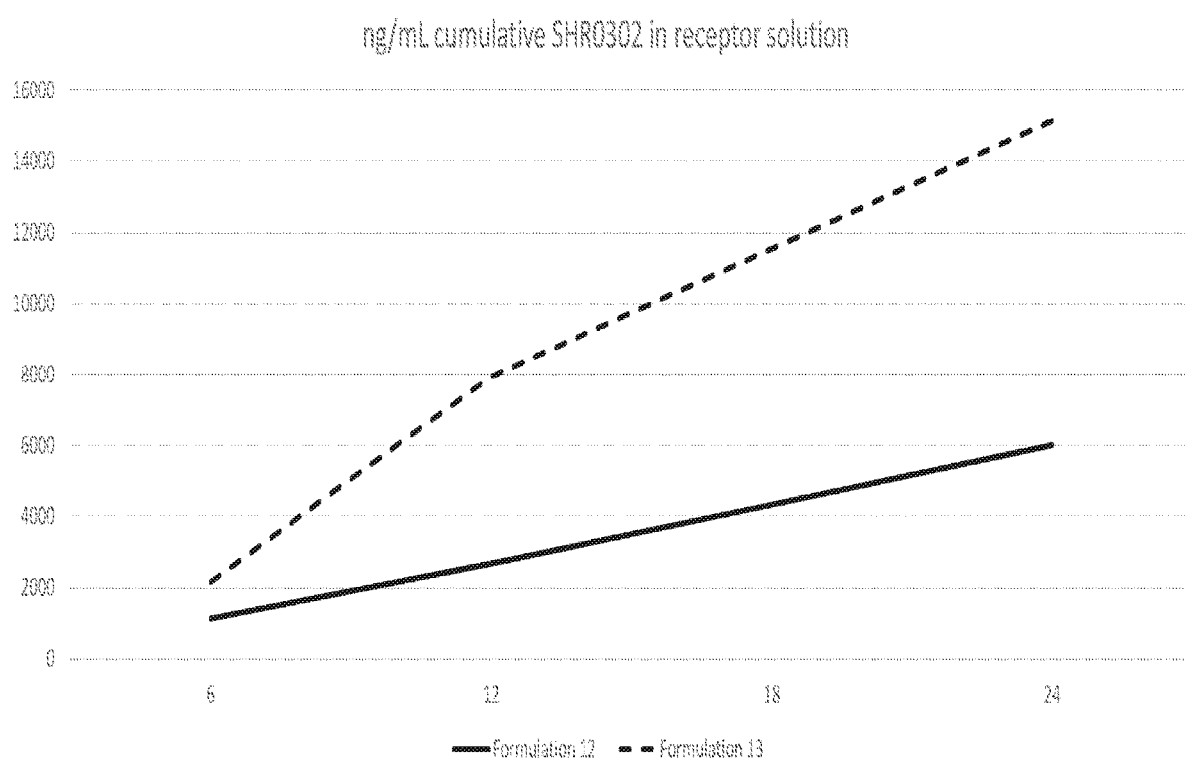
FIG. 6 illustrates IVPT results comparing an exemplary SHR0302 formulation with and without laureth-4. The x-axis depicts time (in hours) and the y-axis depicts ng/mL cumulative SHR0302 in receptor solution. The results show that the addition of laureth-4 significantly enhances the skin penetration effect in formulations containing SHR0302.

The results of this experiment (reported as ng/mL cumulative SHR0302 in receptor solution) are shown in Table 6 and depicted in FIG. 6. The addition of laureth-4 to the topical formulation containing DMSO showed a surprising and striking increase in skin penetration when compared to a nearly identical formulation without laureth-4. These results demonstrate the efficacy of laureth-4 as a skin penetration enhancer in the inventive topical formulations.

TABLE 6

| Formulation # | 1 hr | 3 hr | 6 hr | 12 hr | 24 hr | Epidermis 24 hr | Dermis 24 hr |
|---|---|---|---|---|---|---|---|
| 12 | 11.6 | 272.4 | 1139.6 | 2674.4 | 6008.9 | 2587 | 1899 |
| 13 | 3.6 | 324.2 | 2168.5 | 7943.5 | 15,136.0 | 2133 | 3178 |

Example 13

Formulations of the following compositions were prepared:

| Ingredients | Formulation #7 (2020-092-47) % w/w | Formulation #9 (2020-092-61) % w/w |
|---|---|---|
| SHR0302 | 0.5 | 0.5 |
| Sodium Phosphate Monobasic, Anhydrous | 0.5 | 0.5 |
| Glycerin | — | 5.0 |
| Methylparaben | 0.1 | 0.1 |
| Propylparaben | 0.02 | 0.02 |
| Butylated hydroxytoluene | — | 0.05 |
| Dimethyl Sulfoxide | 10.0 | 10.0 |
| Dimethyl Isosorbide | 10.0 | 10.0 |
| Diethylene glycol monoethyl ether | 10.0 | 10.0 |
| Polysorbate 60 | 10.0 | — |
| Xanthan Gum | — | 0.2 |
| Hydroxyethyl Cellulose | 0.5 | — |
| Laureth 4 | 4.0 | 4.0 |
| Crodafos CES | 10.0 | — |
| Polyethylene (2) stearyl ether | — | 5.0 |
| Polyethylene (21) stearyl ether | — | 5.0 |
| Cetostearyl Alcohol | — | 6.0 |
| White Petrolatum | 10.0 | — |
| PPG 15 Stearyl Ether | — | 5.0 |
| Dimethicone, 350 cst | 1.0 | — |
| Purified Water | Q.S. to 100 | Q.S to 100 |

Formulation #7 was prepared as follows: 38.93 grams of purified water was charged to the main manufacturing vessel. 0.50 grams of sodium phosphate monobasic, anhydrous was added to the water in the main manufacturing vessel and mixed until a clear solution was obtained. In a separate container labeled "Part B" 10.04 grams dimethyl sulfoxide, 10.16 grams of diethylene glycol monoethyl ether (Transcutol P®) and 10.14 grams dimethyl isosorbide were blended together. Two preservatives (0.10 grams of methylparaben and 0.021 grams of propylparaben) and 0.62 grams of the JAK inhibitor SHR0302 were added to "Part B" and stirred until completely dissolved. The entire contents of the container labeled "Part B" was added to the main manufacturing vessel and mixed until a clear solution was obtained. Polysorbate 60 was added (10.15 grams) to the main manufacturing vessel and mixed to form a hazy viscous liquid. Hydroxypropyl cellulose (0.51 grams) was added to the main manufacturing vessel and mixed to form a hazy viscous liquid. In a separate container labeled "Part E" 10.15 white petrolatum, 10.16 grams Crodafos™ CES, and 4.0 grams laureth-4 were combined and heated to 66° C. The main manufacturing vessel was heated to 68° C. Using a homogenizer (25 mm head set at 10,230 rpm) the entire contents of "Part E" were added to the main manufacturing vessel and homogenized for 5 minutes. Dimethicone (1.01 grams) was added to the main manufacturing vessel and homogenized for 2 additional minutes. Purified water (0.76 grams) was added to Q.S. ad the batch to 100%.

Formulation #9 was prepared as follows: 38.63 grams of purified water was charged to the main manufacturing vessel. Glycerin (5.1 grams) and 0.50 grams of sodium phosphate monobasic, anhydrous was added to the water in the main manufacturing vessel and mixed until a clear solution was obtained. Xanthan gum (0.2 grams) was added to the main manufacturing vessel and mixed for 59 minutes. In a separate container labeled "Part D" 10.08 grams dimethyl sulfoxide, 10.10 grams of diethylene glycol monoethyl ether (Transcutol P®), 10.06 grams dimethyl isosorbide 0.10 grams methylparaben, 0.020 grams propylparaben, 0.052 grams butylated hydroxytoluene and 0.62 grams of the JAK inhibitor SHR0302 were combined and mixed until forming a clear solution. In a third separate container labeled "Part C" 5.15 grams Polyethylene (2) stearyl ether, 5.06 grams Polyethylene (21) stearyl ether, 5.06 grams PPG 15 stearyl ether, 6.10 grams cetostearyl alcohol and 4.06 grams laureth-4 were combined and heated to 72° C. The main manufacturing vessel was heated to 74° C. Using a homogenizer (25 mm head set at 9800 rpm) the entire contents of "Part C" were added to the main manufacturing vessel and homogenized for 3 minutes. With continuous homogenization, the entire contents of "Part D" were slowly added to the main manufacturing vessel. Total homogenization time was 5 minutes. Additional purified water for this specific batch was not used to Q.S. ad the batch to 100%.

The foregoing description has been presented for purposes of illustration and description. This description is not intended to limit the invention to the precise form disclosed. Persons of ordinary skill in the art will appreciate that modifications and substitutions of the basic inventive description may be made.

What is claimed is:

1. A method for preparing a topical pharmaceutical composition comprising:
    combining SHR0302, water, and at least one solvent with laureth-4, wherein the topical pharmaceutical composition does not contain an additional active ingredient.
2. The method of claim 1, wherein the amount of laureth-4 is sufficient to improve the skin penetration of SHR0302 relative to the same topical pharmaceutical composition without laureth-4.
3. The method of claim 2, wherein the SHR0302 is present in an amount of about 0.1 to about 1.0% w/w.
4. The method of claim 3, wherein the laureth-4 is present in an amount of about 0.5 to about 5% w/w.
5. The method of claim 3, wherein the laureth-4 is present in an amount of about 1% to about 4%.
6. The method of claim 4, wherein the solvent is dimethyl sulfoxide.
7. The method of claim 6, wherein said composition is selected from the group consisting of an oil-in-water emulsion, a water-in-oil emulsion, a microemulsion, a nanoemulsion, a foam, a spray, a hydrophilic ointment, or a hydrophobic ointment.

8. A method for preparing a topical SHR0302 pharmaceutical composition having improved skin penetration, comprising:
    combining SHR0302, water, and at least one solvent with laureth-4,
    wherein the amount of laureth-4 is sufficient to improve the skin penetration of SHR0302 by 5-fold to 30-fold relative to the same topical pharmaceutical formulation without laureth-4 as measured by in vitro permeation testing in excised human cadaver skin dermatomed to a target thickness of 500 microns, wherein the topical pharmaceutical composition does not contain an additional active ingredient.

9. The method of claim 6, wherein the SHR0302 is present in an amount of about 0.1 to about 1.0% w/w.

10. The method of claim 7, wherein the laureth-4 is present in an amount of about 0.5 to about 5% w/w.

11. The method of claim 7, wherein the laureth-4 is present in an amount of about 1% to about 4%.

12. The method of claim 8, wherein the solvent is dimethyl sulfoxide.

13. The method of claim 10, wherein said composition is selected from the group consisting of an oil-in-water emulsion, a water-in-oil emulsion, a microemulsion, a nanoemulsion, a foam, a spray, a hydrophilic ointment, or a hydrophobic ointment.

14. The method of claim 13, wherein the amount of laureth-4 is sufficient to improve the skin penetration of SHR0302 by 10-fold to 30-fold relative to the same topical pharmaceutical formulation without laureth-4 as measured by in vitro permeation testing in excised human cadaver skin dermatomed to a target thickness of 500 microns.

* * * * *